United States Patent [19]
Collins et al.

[11] Patent Number: 6,045,578
[45] Date of Patent: Apr. 4, 2000

[54] OPTICAL TREATMENT METHOD

[75] Inventors: Michael John Collins; Christine Frances Wildsoet, both of Queensland, Australia

[73] Assignee: Queensland University of Technology, Brisbane, Australia

[21] Appl. No.: 08/849,196

[22] PCT Filed: Nov. 28, 1995

[86] PCT No.: PCT/AU95/00794

§ 371 Date: Sep. 29, 1997

§ 102(e) Date: Sep. 29, 1997

[87] PCT Pub. No.: WO96/16621

PCT Pub. Date: Jun. 6, 1996

[51] Int. Cl.[7] .................................................. A61F 2/16
[52] U.S. Cl. ............................................... 623/6; 128/898
[58] Field of Search ............................. 623/6; 351/160 R, 351/161, 160 H; 128/898

[56] References Cited

U.S. PATENT DOCUMENTS

| | | | |
|---|---|---|---|
| 4,883,350 | 11/1989 | Muckenhirn | 351/160 R |
| 4,909,621 | 3/1990 | Evans | 351/161 |
| 4,957,506 | 9/1990 | Mercier | 623/6 |

*Primary Examiner*—David H. Willse
*Assistant Examiner*—Kelly O'Hara
*Attorney, Agent, or Firm*—Kyle W. Rost

[57] ABSTRACT

Paraxial rays and marginal rays entering the eye do not share a common point of focus in emmetropes, adults usually having a slightly positive spherical aberration. There is provided a method of treatment and prevention of myopia by inducing positive spherical aberration in the myopic eye. The cornea 30 of a myopic eye 31 is fitted with a lens 32 having its outer surface 34 formed having increasing dioptric power away from the axis 35 of the lens and cornea 30. Paraxial light rays 36 entering the central portion 37 of the lens 32 are focused on the retina 40 of the eye 31, producing a clear image of an object. Marginal light rays 41 entering the peripheral portion 42 of the cornea 30 are focused in a plane between the cornea 30 and the retina 40, and produce positive spherical aberration of the image on the latter. This positive spherical aberration produces a physiological effect on the eye which tends to inhibit growth of the eye, thus mitigating the tendency for the myopic eye to grow longer. Methods of treatment of hyperopia, and methods for prevention of focusing disorders based on the same principles are also provided.

13 Claims, 4 Drawing Sheets

OPTICAL TREATMENT METHOD

This invention relates to an optical treatment method.

This invention has particular but not exclusive application to the treatment of focusing disorders of the human eye, and for illustrative purposes reference will be made to such application. However, it is to be understood that this invention could be used in other applications such as to prevent the progression of focusing disorders of the eye such as myopia and hyperopia.

Common conditions which lead to reduced visual acuity are myopia and hyperopia, for which correctional lenses in the form of spectacles, or rigid or soft contact lenses, are prescribed. The conditions are generally described as the imbalance between the length of the eye and the focus of the optical elements of the eye, myopic eyes focusing in front of the retinal plane and hyperopic eyes focusing behind the retinal plane. Myopia typically develops because the axial length of the eye grows to be longer than the focal length of the optical components of the eye, that is, the eye grows too long. Hyperopia typically develops because the axial length of the eye is too short compared with the focal length of the optical components of the eye, that is, the eye does not grow enough.

The corrective lenses are used to alter the gross focus of the eye to render a clearer image at the retinal plane, by shifting the focus from in front of the plane to correct myopia, or from behind the plane to correct hyperopia, respectively. However, the corrective approach to the conditions does not address the cause of the condition but is merely prosthetic.

Most eyes do not have simple myopia or hyperopia, but have myopic astigmatism or hyperopic astigmatism. Astigmatic errors of focus cause the image of a point source of light to form as two mutually perpendicular lines at different focal distances. In the foregoing discussion, the terms myopia and hyperopia are used to include simple myopia or myopic astigmatism and hyperopia and hyperopic astigmatism respectively.

In normal or emmetropic adult eyes, light from both distant and close objects and passing through the central or paraxial region of the aperture or pupil is focused by the crystalline lens inside the eye close to the retinal plane where the inverted image is sensed. It is observed however that most normal eyes exhibit a positive longitudinal spherical aberration, generally in the region of about +0.50 Diopters (D) for a 5 mm aperture, meaning that rays passing through the aperture or pupil at its periphery are focused +0.50 D in front of the retinal plans when the eye is focused to infinity. As used herein the measure D is the dioptric power, defined as the reciprocal of the focal distance of a lens or optical system, in meters.

The spherical aberration of the normal eye is not constant. For example, accommodation, that is, the change in optical power of the eye derived primarily through change to the internal crystalline lens causes the spherical aberration to change from positive to negative.

Emmetropisation is the process whereby eye growth is self-regulated to achieve an optimum match between the optics and axial length of the eye. Emmetropisation is responsible for the leptokurtosis apparent in refractive error distribution in humans and has been demonstrated to act in various animals to compensate for visual deprivation induced refractive errors. Juvenile-onset myopia is a common form of refractive error beginning in childhood and progressing up until the mid to late teens.

Whilst the length of the eye increases throughout life, growth is most pronounced during childhood. It has been observed that spherical aberration of the eye changes with age in children (Stine, 1930; Jenkins, 1963), from negative spherical aberration in children younger than about 6 years of age when focused on distant objects, to positive spherical aberration at about 6–7 years of age. Most adults display positive spherical aberration of the eye focussed at infinity for the remainder of their lives.

It is proposed that the emmetropisation process can be regulated by the effect of spherical aberration on eye growth. Particularly, it is proposed that emmetropisation is controlled by spherical aberration and that, for example, young myopes have higher levels of negative spherical aberration than emmetropes, which promotes inappropriate eye growth.

It is thus an object of the present invention to provide methods for the treatment and/or prevention of refractive error of the eye, and apparatus therefor.

With the foregoing and other objects in view this invention in one aspect resides broadly in a method of altering the focus of the eye including changing the spherical aberration of the retinal image by a direction and degree selected to alter the growth in eye length.

The spherical aberration to be altered is preferably the longitudinal spherical aberration, that is, the spherical aberration of the optical system of the eye in the direction of the lens axis. For the purposes of this description, the expression "spherical aberration" is to be taken to mean longitudinal spherical aberration unless otherwise specified, "Positive spherical aberration" refers to spherical aberration resulting in a marginal focus between the paraxial focus and the lens, whereas negative spherical aberration refers to spherical aberration resulting in the marginal focus occurring on the side of the paraxial focus remote from the lens.

Typically, for viewing objects at a far distance through a 5 mm pupil, the adult eye has a spherical aberration of approximately +0.50 D, and it is presumed that the eye length growth feedback mechanism, whatever its mode of action, operates to stop eye length growth at or about this degree of positive spherical aberration. Accordingly it is preferred that myopia be treated by altering the spherical aberration of the eye from the generally negative spherical aberration apparent in the condition, to somewhere in the range of 0–5 D, and preferably as positive as about +0.50 D.

On the other hand, the presence of negative spherical aberration in the retinal image would promote eye growth, particularly during early childhood, and the eye will continue growing until the spherical aberration reaches its final state of approximately +0.50 D, irrespective of whether or not the paraxial focus is ideally on the retinal plane. Accordingly, in an eye that has failed to grow long enough, that is, a hyperopic eye, the introduction of negative spherical aberration may encourage growth in eye length and thereby correct the hyperopia.

If on the other hand a juvenile presents as emmetropic but having a markedly negative spherical aberration, this may be regarded as predictive for the onset of juvenile myopia, and preventative treatment may comprise the alteration of the spherical aberration to be less negative (more positive). Alternatively if the juvenile presents as emmetropic but having markedly positive spherical aberration, this may be regarded as predictive for the onset of juvenile hyperopia, and preventative treatment may comprise the alteration of the spherical aberration to be less positive (more negative).

The means by which the spherical aberration of the eye may be altered in accordance with the present invention may include surgical alteration of the shape of the cornea, implantation of a lens into the eye, spectacle lenses or contact lenses. Preferably, the means for alteration of the spherical aberration comprises a contact lens.

The change in spherical aberration induced by a contact lens on the eye depends upon a number of parameters including the power of the lens, shape of the front and back surfaces of the lens, refractive index of the lens material, corneal radius of curvature and shape, axial length of the eye and pupil size.

Whilst the foregoing methods refer to the effect of variation of spherical aberration on focussing errors in the unaccommodating eye focused at infinity, it is also observed that spherical aberration of the eye varies as a function of accommodation. In the unaccommodated state, the eye normally has about +0.50 D of spherical aberration for average pupil sizes, as observed above. As the level of accommodation increases, the spherical aberration becomes less positive and at a level of accommodation of about 1.00 to 1.50 D the eye has minimal spherical aberration. Higher levels of accommodation produce increasing negative spherical aberration with about −1.00 D of spherical aberration present at an accommodation level of 3.00 D (Ivanoff, 1956; Jenkins, 1963; Tousey and Scolnik, 1949).

The association between near work and myopia development has been proposed for many years. It is now proposed that since near work increases the amount of negative spherical aberration present in the retinal image, more time spent performing close work would encourage axial length growth in children.

Accordingly, in a further aspect there is provided a method for impeding the onset of accommodation induced myopia in children comprising maintaining positive spherical aberration on the subject eye during close work. The amount of benefit derived would depend on the relationship between spherical aberration and accommodation for each subject and the amount of near work undertaken by each subject. Preferably, the degree of positive spherical aberration is selected whereby accommodation demand during close work is also reduced.

In a further aspect, this invention resides in prosthetic lens apparatus of optical characteristics selected to alter the spherical aberration of the retinal image of an eye in a direction and to a degree sufficient to influence eye length growth. The lens may comprise a spectacle lens, or rigid or soft contact lens.

The lens may serve as a corrective lens for focusing errors of the eye as well as altering the spherical aberration of the eye, or alternatively may be plano, that is, of no correcting power for paraxial rays, serving only to alter the spherical aberration of the retinal image.

The spherical aberration in the prosthetic lens may be produced by any desired method, such as by the use of diffraction, or by providing a variation in the refractive index of the material. However, it is preferred that the spherical aberration be introduced by varying the shape of the lens surface or surfaces, such as by using an aspheric surface. For example, an ellipsoidal surface may be selected for ease of manufacture and such that the transition from optical-correction portion to growth-control portion may be gradual. The shaping of the lens to provide for the alteration to the spherical aberration of the retinal image may be by any means known to the art of producing lenses.

In order that this invention may be more easily understood and put into practical effect, reference will now be made to the accompanying drawings which illustrate a preferred embodiment of the invention, wherein.

Figure 1:
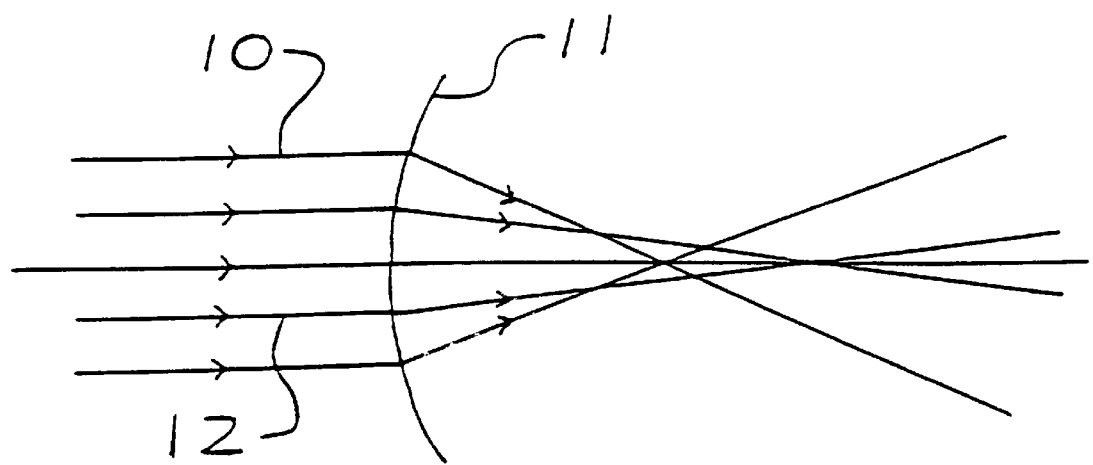
FIG. 1 shows the effect of positive spherical aberration on an eye.
Figure 2:
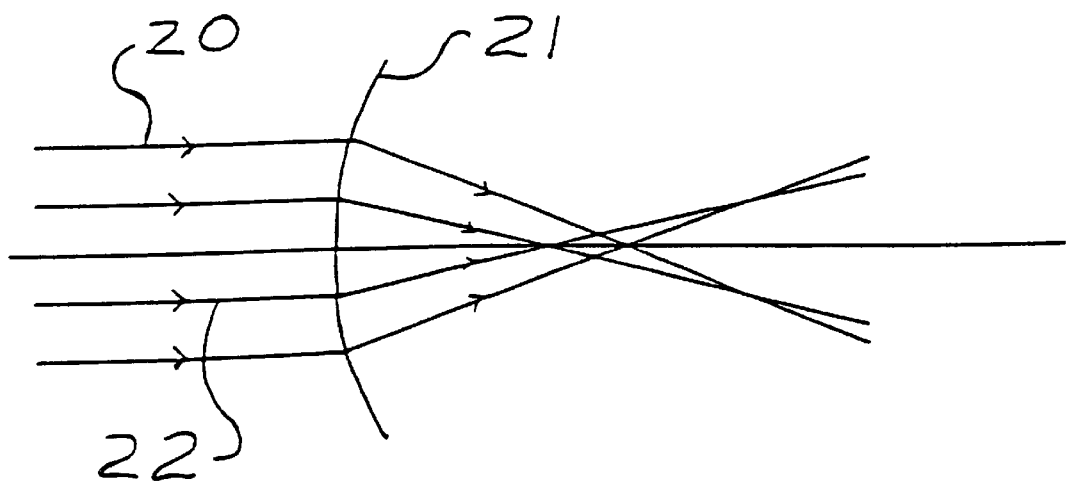
FIG. 2 illustrates the effect of negative spherical aberration on an eye.

Rays of light which enter through the central portion of an eye are termed paraxial rays and rays of light entering through the periphery of a lens are termed marginal or peripheral rays. Spherical aberration occurs when paraxial and marginal rays do not share a common point of focus. As shown in FIG. 1, positive spherical aberration occurs when marginal rays 10 focus closer to the lens 11 than paraxial rays 12. Negative spherical aberration occurs when marginal rays 20 focus further from a lens 21 than paraxial rays 22, as illustrated in FIG. 2.

Figure 3:
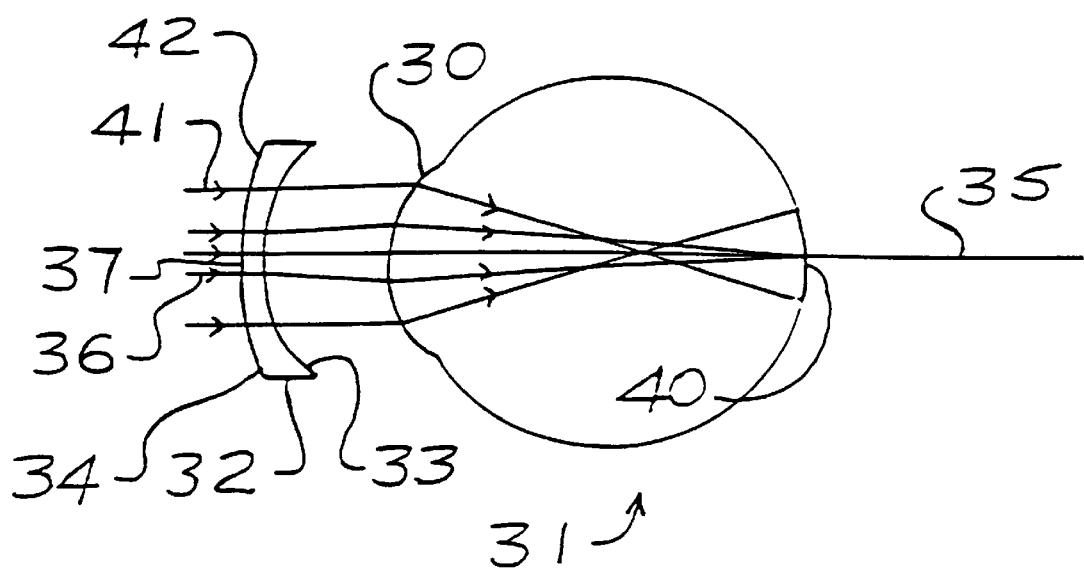
FIG. 3 is a diagram of a myopic eye fitted with a lens having positive spherical aberration.

As shown in FIG. 3, the convex cornea 30 of a myopic eye 31 has been fitted with a lens 32 having its inner surface 33 formed spherically and its outer surface 34 formed as part of an ellipsoid having increasing dioptric power, that is, decreasing radius of curvature, away from the axis 35 of the lens and cornea 30, that is, an oblate ellipsoid. Paraxial light rays 36 entering the central portion 37 of the lens 32 are focused on the retina 40 of the eye 31, producing a clear image of an object. Marginal light rays 41 entering the peripheral portion 42 of the lens 32 and passing to the cornea 30 are focused in a plane between the cornea 30 and the retina 40, and produce positive spherical aberration of the image on the latter. This positive spherical aberration produces a physiological effect on the eye which tends to inhibit growth of the eye, thus mitigating the tendency for the myopic eye to grow longer.

Figure 4:
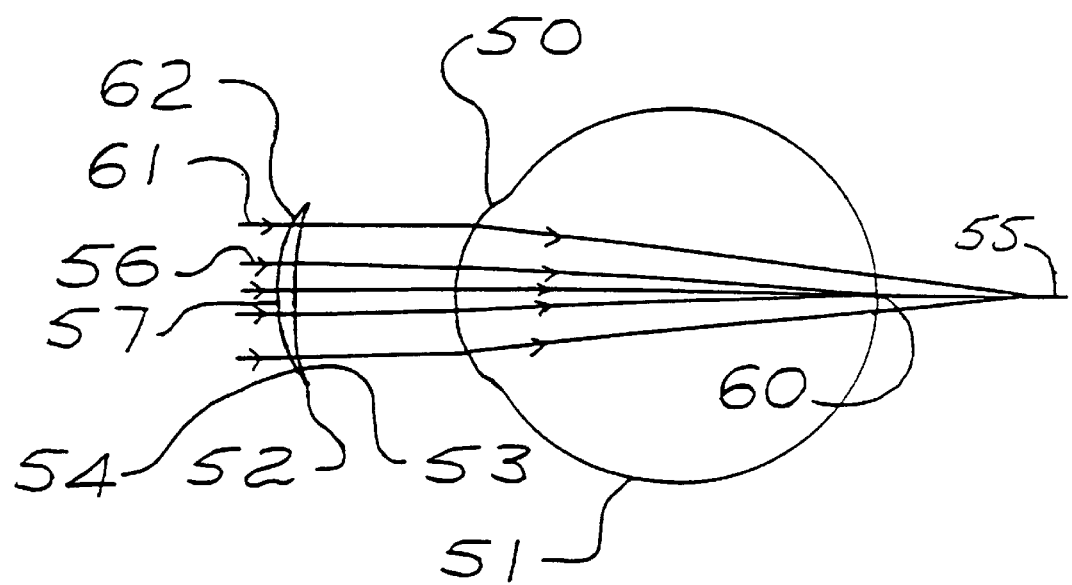
FIG. 4 is a diagram of a hyperopic eye fitted with a lens having negative spherical aberration.

Referring now to FIG. 4, it will be seen that the cornea 50 of a hyperopic eye 51 has been fitted with a lens 52 having its inner surface 53 formed spherically, and its outer surface 54 formed as part of an ellipsoid having decreasing dioptric power, that is, increasing radius of curvature, away from the axis 55 of the lens and cornea 50, that is, a prolate ellipsoid. Paraxial light rays 56 entering the central portion 57 of the lens 52 and passing to the cornea 50 are focused on the retina 60 of the eye 51, producing a clear image of an object. Marginal light rays 61 entering the peripheral portion 62 of the lens and passing to the cornea 50 are focused behind the retina 60, and produce a negative spherical aberration of the image on the latter. This negative spherical aberration produces a physiological effect an the eye which tends to enhance growth of the eye, thus mitigating hyperopia.

In a clinical example, a −3.00 D myopic eye when treated with a spherical prosthetic (contact) lens exhibits corrected focus, with little affect on progression of the myopia. This progression is typically at a rate of about −0.50 D to −0.75 D per year. However, substitution in one eye with a prosthesis having an aspheric front surface in the form of an oblate ellipse, having the same corrective power for paraxial rays as the spherical lens but inducing a positive spherical aberration of +0.75 D on the eye, produces a cessation or slowing of the development of myopia.

It will of course be realised that while the above has been given by way of illustrative example of this invention, all such and other modifications and variations thereto as would be apparent to persons skilled in the art are deemed to fall within the broad scope and ambit of this invention as defined in the claims appended hereto.

We claim:

1. A method of altering the focus of an eye including changing the spherical aberration of the retinal image by a direction and degree selected to influence growth in eye length.

2. A method according to claim 1, wherein said spherical aberration is the longitudinal spherical aberration of the eye.

3. A method according to claim 2, wherein said spherical aberration is altered in a positive direction to substantially halt eye length growth.

4. A method according to claim 2, wherein said spherical aberration is altered to be more than about +0.50 D.

5. A method according to claim 2, wherein spherical aberration of the eye is made more negative to promote eye growth.

6. A method according to claim 5, wherein said spherical aberration is altered to be less than about +0.50 D.

7. A method for preventing the onset, or reducing the progression, of myopia in an eye comprising inducing a positive change in the spherical aberration of said eye.

8. A method in accordance with claim 7, wherein said positive change is sufficient to alter the spherical aberration of the eye to about +0.50 D.

9. A method for treating hyperopia in an eye comprising inducing a change in the spherical aberration of said eye to below about +0.50 D to influence growth in eye length.

10. A method in accordance with any one of claims 1 to 9, wherein alteration of the spherical aberration is by prosthetic means selected from implanted lenses, spectacles and contact lenses, or surgical means.

11. A method for impeding the onset of accommodation induced myopia comprising maintaining positive spherical aberration in an eye during close work being done by the eye.

12. A method according to claim 11, wherein said positive spherical aberration is further selected to reduce accommodation demand under close work conditions.

13. Prosthetic lens apparatus, wherein said lens is plano for paraxial rays and wherein said lens changes the spherical aberration of the retinal image of an eye by a direction and degree selected to influence growth in eye length.

* * * * *